United States Patent [19]

Thornton et al.

[11] Patent Number: 5,415,735
[45] Date of Patent: May 16, 1995

[54] RECOVERY OF ORGANIC SUBSTANCES DISSOLVED IN MECHANICAL PULP

[75] Inventors: Jeffrey Thornton; Rainer Ekman; Bjarne Holmbom; Christer Eckerman, all of Turku; Maij Tenkanen, Espoo; Liisa Viikari, Helsinki, all of Finland

[73] Assignee: Metsa-Serla Oy, Helsinki, Finland

[21] Appl. No.: 92,853

[22] Filed: Jul. 19, 1993

[30] Foreign Application Priority Data

Jul. 17, 1992 [FI] Finland .................... 923269

[51] Int. Cl.⁶ ............................ D21C 3/20
[52] U.S. Cl. ...................... 162/72; 162/19; 162/190; 435/101; 435/196; 435/278; 435/913
[58] Field of Search ............... 162/72 B, 19, 190; 435/101, 278, 196, 913

[56] References Cited

U.S. PATENT DOCUMENTS 3,406,089 10/1964 Yerkes, Jr. .................... 435/278

FOREIGN PATENT DOCUMENTS 0430915 5/1991 European Pat. Off. .

OTHER PUBLICATIONS

Holmbom et al. "Chemical Changes in Peroxide Bleaching of Mech Pulp" Das Papier, 45. Jahrgang, Heft 10A, 1991, pp. 16–22.
Tenkanen et al., "Production, Purification . . . Lignocellulosic", Jnl of Biotechnology, 18 (1991), pp. 69–84.
Thornton, Jeff, "Effects of Peroxide . . . Organic Substances", 6th Int. Symp of Pulping & Wood Chem, Australia 1991, pp. 1–7.
Lafend K. B., "Effect of Acetyl Content . . . Properties", TAPPI vol. 51, No. 3, Mar. 1968, pp. 118–123.
"Chemical Changes in Peroxide Bleaching of Mechanical Pulps", Thornton et al., Das Papier, 45.Jahrgang, Heft 10A, 1991, pp. 16–22.
"Sorption of Hemicelluloses on Cellulose Fibres" Hansson, Holzforschung 24 (1970) H. 3, pp. 77–83.
"The Influence on Paper Strength . . . " Lindstrom et al., Svensk Papperstidn. 80(11):341–345, 1977.
"Production, purification and characterization . . . ", Jnl. of Biotechnology, 18 (1991), pp. 69–84.

Primary Examiner—Peter Chin
Assistant Examiner—Dean T. Nguyen
Attorney, Agent, or Firm—Adduci, Mastriani, Schaumberg & Schill

[57] ABSTRACT

This invention relates to a method for the recovery of organic substances dissolved or brought into a colloid form during the manufacture of a mechanical pulp where said mechanical pulp has not been subject to previous alkaline bleaching or other previous process carried out under alkaline conditions. The method is characterized in the deacetylation of the galactoglucomannans having been brought into dissolved or colloidal form during the pulping process, and subsequent deposition of said deacetylated glucomannans onto a solid phase, such as pulp fibers or organic or inorganic additives. The deacetylation is performed either by alkali or enzymatically. The method diminishes the organic substance loading on recycling waters and effluents, and improves the yield and strength properties of the pulp.

6 Claims, No Drawings

RECOVERY OF ORGANIC SUBSTANCES DISSOLVED IN MECHANICAL PULP

This invention relates to a novel method for the treatment of mechanical pulps which have not previously undergone alkaline treatment e.g. in connection with peroxide bleaching. The method results in improved yield and quality of said pulps. The method further gives rise to a decrease in dissolved and colloidal substances (DCS) in the backwater.

The most important mechanical pulp qualities are thermomechanical pulp (TMP), groundwood (SGW), pressurized groundwood (PGW), refiner mechanical pulp (RMP), pressurized refiner mechanical pulp (PRMP) and chemithermomechanical pulp (CTMP). The mechanical pulps are mostly prepared from softwood. The mechanical pulps distinguish from chemical pulps mainly with respect to the high yield which is achieved as a result of the lignin and carbohydrate-saving pulping method. Chemical pulps, from which substantial amounts of the lignin and hemicellulose components have been removed, have a high percentage of cellulose compared to that of mechanical pulps, and have therefore strength qualities superior to those of mechanical pulps.

The main use of mechanical pulps is cheaper paper qualities of relatively short-term usage, particularly newsprint. Traditionally newsprint has been made of approximately 80% groundwood and 20% chemical pulp. More recently, the introduction of mechanical pulp qualities of improved strength properties such as TMP, PRMP and PGW have made it possible to considerably decrease the amount of chemical pulp in newsprint. These mechanical pulps are also of great importance in various kinds of other printing papers such as journal paper grades.

Most of the mechanical pulps for printing papers are either used as unbleached or are bleached under very mild conditions in order to save as much of the pulp substance as possible. A usual bleaching method for mechanical pulps is the dithionite method, a process carried out at about pH 5 to 6. Another usual process for bleaching mechanical pulps is the bisulphite method, which is carried out at a pH of about 4.

Peroxide bleaching, although classified as a wood saving method, causes a higher loss of yield than the dithionite and bisulphite methods, but on the other hand it gives higher brightness. Peroxide bleaching of TMP has been subject to extensive research work and it has also to some extent replaced the above mentioned bleaching methods for TMP because this pulp has partially replaced chemical pulp in many paper grades. Peroxide bleaching is, contrary to the afore mentioned methods, carried out in alkaline conditions, pH 10.5 to 11.

However, the main part of mechanical pulps today are either used unbleached or are bleached under methods of slightly acidic conditions.

Softwoods contain about 20–25% mannans consisting of a glucomannan backbone to which acetyl groups and galactose residues are attached. These polyoses are called O-acetylgalactoglucomannans and a partial structure of such a polyose is illustrated as follows:

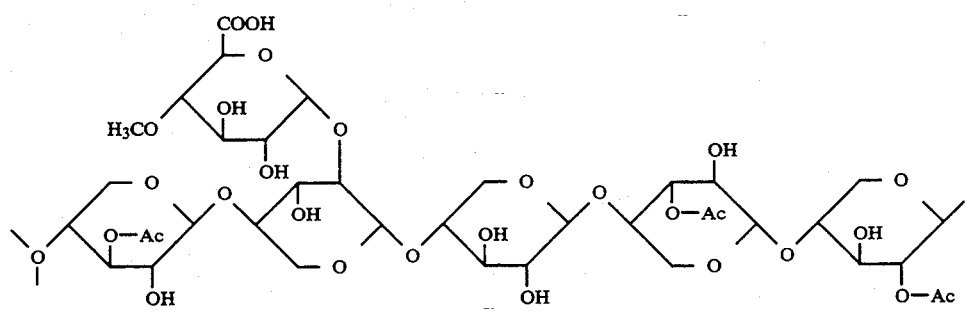

Deacetylation of glucomannans, has been observed in connection with the alkaline conditions during studies with peroxide bleaching of mechanical pulp, particularly TMP. Such results have been reported by J Thornton et al "Effects on peroxide bleaching on spruce TMP on dissolved and colloidal organic substances" presented at the 6th Int. Symp. of Pulping and Wood Chem., Melbourne, Australia, May 7th, 1991. An article by B Holmbom et al, "Chemical Changes in Peroxide Bleaching of Mechanical Pulps", Das Papier, 45. Jahrgang, Heft 10A, 1991, pp 16–22 also reported a deacetylation of glucomannans after the alkaline peroxide bleaching process. The same reference disclose that the deacetylation of galactoglucomannans dissolved in the pulp suspension leads to their adsorption onto the pulp fibers and thus to a recovery in pulp yield of about 1%. Previous studies Laffend, K. and Swenson, H., Tappi 51(3)118–123(1968) and Hansson, J-Å., Holzforschung 24 (1970) H.3, pp 77–83) have reported the adsorption of hemicelluloses onto cellulose fibers, and the improvement of adsorption due to deacetylation of the glucomannan. Lindström T. et al, Svensk Papperstidn. 80(11):341–345, 1977, reported on improvements of strength in pulps to which hemicelluloses and fines have been added.

To sum up, from peroxide bleaching of mechanical pulp under alkaline conditions it is known that such alkaline conditions cause deacetylation of dissolved and colloidal galactoglucomannans derived from the pulping process, and that such deacetylated galactoglucomannans adsorb onto the fibers resulting in an improved yield.

This invention is based on the idea to utilize this phenomenon, the deacetylation of the galactoglucomannans, to recover organic dissolved or colloidal substances originating from the mechanical pulping process where the mechanical pulp has not been subject to any previous alkaline treatment such as peroxide bleaching. No such use of the deacetylation of galactoglucomannans has been suggested before although there exists a great need to improve pulp yields and to diminish the organic substance loading on recycling waters and effluents. This invention is applicable to the main part of all mechanical pulps manufactured, because as said above, the main part of these pulps has been subject to only mild bleaching under acidic conditions or no bleaching at all, and accordingly, not undergone any alkaline treatment. The invention is not intended for use with mechanical pulps that are bleached with e.g. peroxide under alkaline conditions, because deacetylation takes place automatically during the alkaline bleaching process.

The object of the present invention is a method for the recovery of organic substances dissolved or brought into a colloid form during the manufacture of a mechanical pulp where said mechanical pulp has not been subject to previous alkaline bleaching or other previous process carried out under alkaline conditions. A characteristic feature of the method is the deacetylation of the galactoglucomannans having been brought into dissolved or colloidal form during the pulping process and subsequent deposition of said deacetylated glucomannans onto a solid phase.

The deposition of the deacetylated glucomannans can take place on any solid component in the system, e.g. on a fiber from the same mechanical pulp; another mechanical, semichemical or chemical pulp fiber; or an organic or inorganic additive. The fibers can be virgin or recycled.

The deacetylation of the galactoglucomannans can be carried out directly on the pulp suspension. However, according to a preferred embodiment, the backwater is separated from the pulp suspension first. Then the deacetylation is performed on the galactoglucomannans in the backwater. After the deacetylation of the glucomannans the backwater is returned to a mixture comprising pulp of one or more grades and optionally organic or inorganic additives. In case the backwater is returned to the same mechanical pulp from which the the dissolved or colloidal glucomannans originated, the deposition of the deacetylated glucomannans on the pulp fibers will lead to increased strength of that pulp grade. The treatment of the backwater instead of the whole pulp suspension leads to more uniform process conditions, and moreover, the deacetylation chemicals are prevented from acting adversely on the pulp fibers.

The deacetylation can be performed either under alkaline conditions or under the influence of an enzyme or enzyme mixture deacetylating the glucomannans.

Suitable enzymes to be used are esterases or enzyme mixtures containing esterase activity, specifically acetyl esterase activity. Most preferable are those having acetyl-glucomannan esterase activity. The process can be carried out in the pH range of 3 to 8, but the most preferable pH range is 5 to 6. The temperature can vary within the range 20° to 90° C., preferably 50° to 70° C. The dose ranges from 0.01 to 100 000 μg esterase/mg DCS glucomannans.

In case the process is performed under the influence of alkali, the pH is kept in the range of 8.5 to 12, preferably 9 to 9.5, and the temperature ranges from 40° to 90° C. preferably 50° to 70° C. In case the deacetylation is performed under alkaline conditions on the backwater, the pH is preferably adjusted to about 5 to 6 with the addition of an acidifying agent, e.g. HCl, if necessary before the backwater is returned to the pulp. It is known that certain miscoloring of the pulp take place under influence of alkali, and this must be avoided for pulps intended for paper grades of high brightness requirements.

The invention is presented in more detail in the examples below. In these studies, two methods of selectively deacetylating dissolved and/or colloidal glucomannans were investigated. In the first example the deacetylation was carried out utilizing alkaline conditions. In the second example an enzyme was used that had glucomannan deacetylating esterase activity, see Journal of Biotechnology, 18 (1991), 69–84. Both methods were successful in lowering the amount of dissolved and colloidal organic substances. Example 1 and 2 describe the experiments, respectively.

EXAMPLE 1

A 1% suspension of TMP from Norway spruce was made according to the standard method disclosed in the article by J. Thornton et al "Effects on peroxide bleaching on spruce TMP on dissolved and colloidal organic substances" presented at the 6th Int. Symp. of Pulping and Wood Chem., Melbourne, Australia, May 7th, 1991. This suspension was vacuum dewatered using a 200-mesh wire and the resulting filtrate passed back through the mat to collect as much fines as possible. The dewatered pulp was set aside. The fines-free filtrate was then alkaline treated with 20 mmol NaOH per liter of filtrate at 60° C. for 30 min. The filtrate pH was then lowered back to 5.5 by adding HCl. After acidification, the alkaline treated filtrate was then mixed together with the dewatered pulp. The 1% suspension was allowed to mix for 90 min at 60° C. and the fibers were then centrifuged away. Standard analyses were then made on the resulting fiber and fines-free supernatant. A blank analysis was performed with no NaOH added as a comparison. The results are presented in Table 1 below:

TABLE 1

Results from alkaline deacetylation experiment

| | Non-treated | Alkaline-treated | Percent change |
|---|---|---|---|
| TOC, mg/l | 234.8 | 175.3 | −25% |
| Carbohydrates, mg/l | 183.6 | 108.9 | −41% |

In the tables the abbreviation TOC means total organic carbon. These results show a decrease in about 60 mg/l TOC, which is about 120 mg/l organic material (assuming 50% carbon). This translates into a yield increase of 120 mg/l/10000 mg fiber/l*100=1.2%. This is a very significant yield increase. This also shows that the water after alkaline treatment is cleaner, therefore requiring less money to treat the waste leaving the mill. As discussed earlier, other benefits may follow from such a treatment. The 41%. decrease in carbohydrates can be attributed to galactoglucomannans.

EXAMPLE 2

The same 1% TMP suspension as used in the previous example was made for this example. A 20 ml aliquot was put in a test tube. 200 μl of the acetyl esterase glucomannan deacetylating enzyme was added to the 20 ml suspension and the tube was capped, thoroughly shaken, and placed in a 40° C. water bath. Constant mild shaking was used to keep the tube contents thoroughly mixed throughout the 16 h reaction time. The contents of the tube were then centrifuged (as in Example 1) and the supernatant analyzed as in Example 1. A blank analysis was performed with no enzyme added. The results obtained are presented below in Table 2.

TABLE 2

Results from enzymatic deacetylation experiment

|  | Non-treated | Enzyme-treated | Percent change |
|---|---|---|---|
| TOC, mg/l | 229.0 | 186.0 | −19% |
| Carbohydrates, mg/l | 190.9 | 138.8 | −27% |

Although not as favorable as the alkaline treatment, this clearly shows that enzymatic deacetylation is a possible method to use for this invention. The decreased carbohydrates were galactoglucomannans. The calculated yield increase was about 0.9%. Still a very significant yield increase. The benefits of this treatment are that no corrosive salts are formed as in the alkaline-deacetylation method. Further research will lead to improved enzyme preparations that will work more effectively at mill conditions.

We claim:

1. A method for the recovery of organic substances dissolved or brought into colloid form during the manufacture of a mechanical pulp, said mechanical pulp not having been subjected to previous alkaline bleaching or other process carried out under alkaline conditions, comprising:

providing a suspension of mechanical pulp containing galactoglucomannans in dissolved or colloid form and, optionally, suspended solid additives, chemically deacetylating the galactoglucomannans using an esterase enzyme or enzyme mixture containing esterase activity in the absence of a peroxide to produce deacetylated glucomannans, and depositing the deacetylated glucomannans onto pulp fibers.

2. A method according to claim 1 wherein the pulp fiber is a fiber from the same mechanical pulp or another mechanical, semichemical or chemical pulp.

3. A method according to claim 1 wherein the enzyme or enzyme mixture has acetyl esterase activity.

4. A method according to claim 3 wherein the enzyme or enzyme mixture has acetyl-glucomannan esterase activity.

5. A method according to claim 1 or 2 wherein the pulp suspension is treated to form a back water containing said galactoglucomannans in dissolved or colloid form, deacetylation is performed on the galactoglucomannans in the back water and the back water after the deacetylation is returned to a mixture comprising pulp of one or more grades and optionally organic or inorganic additives.

6. A method according to claim 5 wherein the pH is adjusted to about 5 to 6 with the addition of an acidifying agent before the back water is returned to the pulp.

* * * * *